United States Patent
Kurita et al.

(10) Patent No.: US 7,812,614 B2
(45) Date of Patent: Oct. 12, 2010

(54) ELECTRON CAPTURE DETECTOR AND NONRADIATIVE ELECTRON CAPTURE DETECTOR

(75) Inventors: Shinji Kurita, Hitachiota (JP); Norio Kawamura, Hitachinaka (JP); Masahiro Takeuchi, Tokyo (JP)

(73) Assignee: Hitachi High-Tech Science Systems Corporation, Hitachinaka-shi (JP)

( * ) Notice: Subject to any disclaimer, the term of this patent is extended or adjusted under 35 U.S.C. 154(b) by 257 days.

(21) Appl. No.: 11/664,257

(22) PCT Filed: Oct. 27, 2005

(86) PCT No.: PCT/JP2005/019822
§ 371 (c)(1),
(2), (4) Date: Mar. 30, 2007

(87) PCT Pub. No.: WO2006/046663
PCT Pub. Date: May 4, 2006

(65) Prior Publication Data
US 2007/0296417 A1    Dec. 27, 2007

(30) Foreign Application Priority Data
Oct. 27, 2004   (JP)   ............................ 2004-311868
Feb. 18, 2005   (JP)   ............................ 2005-041836

(51) Int. Cl.
G01N 27/62   (2006.01)
(52) U.S. Cl. ....................................... 324/464; 324/465
(58) Field of Classification Search ................. 324/464, 324/465
See application file for complete search history.

(56) References Cited

U.S. PATENT DOCUMENTS

| | | | | |
|---|---|---|---|---|
| 5,109,248 A | * | 4/1992 | Petrakos et al. | 396/155 |
| 5,394,091 A | * | 2/1995 | Wentworth et al. | 324/464 |
| 5,394,092 A | * | 2/1995 | Wentworth et al. | 324/464 |
| 5,594,346 A | * | 1/1997 | Stearns et al. | 324/464 |
| 6,701,789 B1 | * | 3/2004 | Denny | 73/700 |
| 2004/0086434 A1 | * | 5/2004 | Gadgil et al. | 422/186.04 |

FOREIGN PATENT DOCUMENTS

JP    4-303759 A    10/1992

(Continued)

OTHER PUBLICATIONS

Collin et al. Ionization Potentials of Some Olefins, Di-olefins and Branched Paraffins, dated Oct. 20, 1958 (published on the internet on May 1, 2002), vol. 81, pp. 2064-2066 (though the full document is 4 pages).*

Barbalace, Period Table of Elements, updated Feb. 22, 2007, EnvironmentalChemistry.com, printout is 3 pages long.*

(Continued)

*Primary Examiner*—Jeff Natalini
(74) *Attorney, Agent, or Firm*—Crowell & Moring LLP

(57) ABSTRACT

It is intended to realize measuring of trace organic components and to render qualitative procedure efficient through imparting of selectivity. Penning gas and dopant gas are ionized in a space isolated from discharge part with the use of metastable helium obtained by direct-current glow discharge, and with the use of thus obtained plasma, the efficiency of ionization of components to be measured is enhanced, so that intensified ion current can be obtained. Further, through selection of dopant gas and Penning gas, selectivity can be imparted. Thus, not only can measuring of trace organic components be performed but also selectivity can be imparted.

8 Claims, 11 Drawing Sheets

FOREIGN PATENT DOCUMENTS

| | | |
|---|---|---|
| JP | 9-507573 A | 7/1997 |
| JP | 9-274015 A | 10/1997 |
| JP | 2004-333187 A | 11/2004 |
| WO | WO 95/10966 | 7/1995 |
| WO | WO 95/18966 A2 | 7/1995 |

OTHER PUBLICATIONS

International Search Report dated Feb. 7, 2006 with English translation (Seven (7) pages).

* cited by examiner

FIG. 6

| Matter | Emission energy (eV) | Ionization energy (eV) |
|---|---|---|
| He | 20.6 | 24.6 |
| Ne | 16.7 | 21.6 |
| Ar | 11.8 | 15.8 |
| $N_2$ | | 15.6 |
| $H_2$ | | 15.4 |
| Kr | 10.6 | 14.0 |
| CO | | 14.0 |
| $CO_2$ | | 13.8 |
| Xe | 9.6 | 13.4 |
| $H_2O$ | | 12.6 |
| Methane | | 12.5 |
| $O_2$ | | 12.1 |
| Carbon tetrachloride | | 11.5 |
| Chloroform | | 11.4 |
| Propane | | 11.0 |
| Methanol | | 10.9 |
| Ethanol | | 10.5 |
| Butane | | 10.5 |
| n-propanol | | 10.2 |
| iso-propanol | | 10.1 |
| n-butanol | | 10.1 |
| n-hexane | | 10.1 |
| n-heptane | | 9.92 |
| n-octane | | 9.82 |
| Acetone | | 9.72 |
| n-decane | | 9.65 |
| n-undecane | | 9.56 |
| Trichloroethylene | | 9.47 |
| Benzene | | 9.25 |
| Tetrachloroethylene | | 9.32 |
| Toluene | | 8.82 |
| p-xylene | | 8.44 |
| Naphthalene | | 8.14 |
| Trimethylamine | | 7.82 |
| Aniline | | 7.72 |
| Triethylamine | | 7.50 |
| Pyrene | | 7.41 |
| N-methylaniline | | 7.33 |
| Diphenylamine | | 7.16 |
| N, N'-dimethylaniline | | 7.12 |
| 1-naphthylamine | | 7.10 |
| $\beta$-carotene | | 6.50 |

FIG. 10 A    Detection limit value (S/N = 3) of γ-BHC : 0.08pg
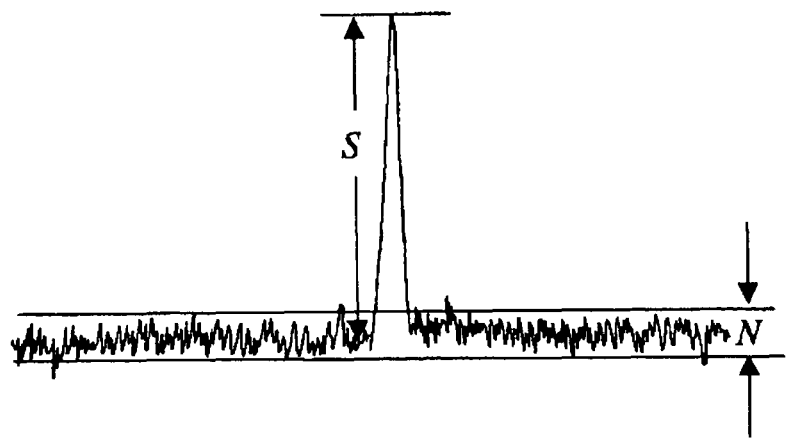
FIG. 10 B    Detection limit value (S/N = 3) of γ-BHC : 10pg
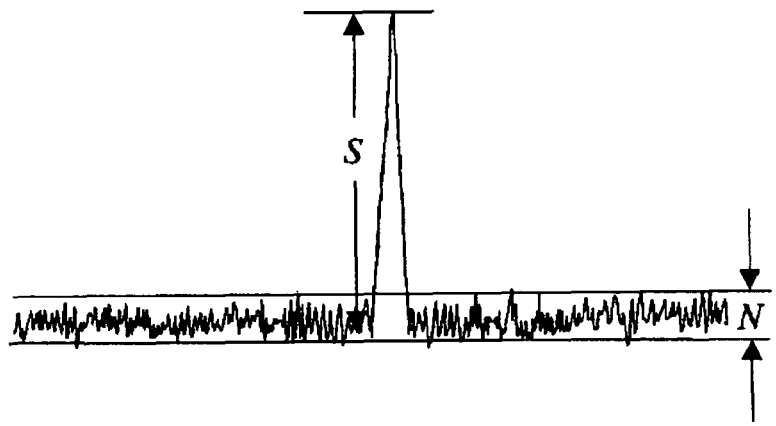

ELECTRON CAPTURE DETECTOR AND NONRADIATIVE ELECTRON CAPTURE DETECTOR

TECHNICAL FIELD

The present invention relates to an electron capture detector for a gas chromatograph, and particularly relates to an electron capture detector generating deep-ultraviolet (deep-UV) rays by generating a discharge in He, ionizing dopant gas by the deep-UV rays, mainly generating negative ions of halogen compound gas using a relatively high electron-density part, and obtaining a signal corresponding to a concentration of a detection target gas using a recombination reaction with ionized positive ions.

The present invention relates to a nonradiative electron capture detector ionizing dopant gas by action of excited helium generated by a glow discharge in helium, measuring a quantity of generated free electrons as a ground current of the detector, and being based on a detection principle of regarding a decrease of the quantity of free electrons based on an electron capture reaction provoked when an electron-affinic detection target component flows into the detector as a decrease of the base current.

BACKGROUND ART

An electron capture detector is employed as a detector for a gas chromatograph. As a detection principle of this electron capture detector, a method using radiation and a method without using radiation are known.

As the electron capture detector without using the radiation, there are known those described in Patent Documents 1 and 2. The electron capture detector described in the Patent Document 1 generates a discharge in He and uses deep-UV rays when $He_2$ returns to a ground state, for generation of plasma (positive ions and electrons).

Furthermore, the electron capture detector described in the Patent Document 2 performs ionization by deep-UV rays generated from a deep-UV lamp.

Because such an electron capture detector does not generate radial rays, the electron capture detector is easy to handle and convenient for outdoor measurement of groundwater, soil gas or the like.

There is known a nonradiative electron capture detector using a discharge phenomenon in rare gas (described in, for example, the Patent Document 1).

As a nonradiative electron capture detector of this type, a photoionized electron capture detector by a pulsed discharge (pulsed-discharge photoionized electron capture detector) as shown in FIG. 8 is known, for example.

With this method, the pulsed discharge causes transition of helium to an excited state (Formula (1)), dopant gas is ionized by UV-rays (Formula (2)) generated when helium in the excited state returns to the ground state (Formula (3)), and the quantity of generated free electrons is measured as the ground current in the detector.

This ground current is a current value when detection target component does not exist in the detector. If an electron-affinic detection target component (M) flows into the detector through a column, an electron capture reaction of the detection target component occurs to decrease the quantity of free electrons in the detector (Formula (4)), with the result that the ground current lowers. A response principle of the detector that such a change in ground current is grasped as a chromatogram is exactly identical to that of a radiative electron capture detector.

$$He \rightarrow He^* \quad \text{Formula (1)}$$

$$He^* \rightarrow He + h\nu \quad \text{Formula (2)}$$

$$Xe \rightarrow Xe^+ + e^- \quad \text{Formula (3)}$$

$$M + e^- \rightarrow M^- \quad \text{Formula (4)}$$

Patent Document 1: Japanese Patent Application National Publication Laid-Open No. 9-507573
Patent Document 2: Japanese Patent Application Laid-Open No. 4-303759

DISCLOSURE OF THE INVENTION

However, in the electron capture detector using a light source lamp or the discharge in He as an ionization source, as disclosed in the Patent Document 1 or 2, inverted peaks that do not occur with a method using a radiation source occur.

Namely, in the electron capture detector without using the radiation source, organic matters in a sample are ionized, and not only peaks by electron capture but also inverted peaks generated by the ionized organic matters when current between detection electrodes temporarily rises are detected.

If the inverted peaks as well as the peaks by the electron capture are detected, it is often judged that a baseline includes the inverted peaks and recognized that one different from an original baseline is the baseline when a data processor perform data processing.

To avoid these problems, a method for displaying detection data and causing an operator to exclude the inverted peaks is possibly used. However, because of manual processing, the method is cumbersome and unfavorable for the data processing.

Furthermore, the method is applicable if the inverted peaks are excludable. However, it is sometimes difficult to discriminate the inverted peaks from the peaks by the electron capture. In this case, it is difficult to exclude the inverted peaks even by the manual processing.

The nonradiative electron capture detector according to the above-stated conventional technique has an advantage of no legal restrictions because the radiation source is not used. On the other hand, the nonradiative electron capture detector is inferior to the radiative electron capture in detection sensitivity and the like. Moreover, the nonradiative electron capture detector has an unsolved problem that inverted peaks of uncertain cause emerge on a chromatogram.

Due to this, an absolute quantity (a detection limit value) of a measurable sample is about 1 ng. Further, the inverted peaks in the chromatogram sometimes become interference peaks against an analysis target component because the reason for emergence remains unclear. As a result, the conventional nonradiative electron capture detector is in a situation in which the detector is difficult to make effective use of.

It is an object of the present invention to realize an electron capture detector that uses a discharge in He, that can suppress generation of inverted peaks generated when current between detection electrodes temporarily rises by ionized organic matters, that has a simple configuration, and that can ensure high sensitivity.

It is an object of the present invention to provide a nonradiative electron capture detector that has performance comparable to that of a radiative electron capture detector, i.e., a detection limit value of 0.1 pg or less, and that eliminates inverted peaks emerging on a chromatogram.

Furthermore, it is an object of the present invention to realize a detector for a gas chromatogram based on a new detection principle obtained as a study result for eliminating the inverted peaks.

To attain the objects, the present invention is constructed as follows.

(1) An electron capture detector comprises a discharge chamber to which helium gas is supplied and which generates deep-ultraviolet rays by a discharge in the helium gas, and a dopant gas source accommodating inactive gas that contains two gas components having different ionization energies from each other, and a detecting tube to which dopant gas is supplied from the dopant gas source, to which column gas serving as a sample is supplied from a gas chromatographic column, which ionizes the dopant gas by the deep-ultraviolet rays, and which detects a signal corresponding to a component of the column gas by recombination reaction with ionized ions.

(2) An electron capture detector comprises a discharge chamber that has a needle-like negative electrode and a ring-shaped positive electrode, in a housing, wherein a stable continuous discharge is generated in a helium stream introduced into the discharge chamber between the negative electrode and the positive electrode, by a direct-current power supply and a series resistance, a detecting tube is constructed by sequentially connecting a first insulating tube, a first ring electrode, a second insulating tube, a second ring electrode, and a third insulating tube downstream of the discharge chamber, both a first filling tube opened toward upstream of the helium stream for introducing inactive gas that contains two trace gas components having different ionization energies from each other as dopant gas, and a second filling tube opened toward upstream of the helium stream for introducing column gas that is a sample separated and introduced from a gas chromatographic column are provided in the detecting tube, an opening of the second filling tube is located between the first ring electrode and the second ring electrode, and the opening of the second filling tube is located downstream of the first filling tube.

(3) In (1) and (2), the two gas components having the different ionization energies from each other are preferably a high-energy component having the ionization energy equal to or higher than 12.0 eV and a low-energy component having the ionization energy equal to or lower than 11.0 eV.

(4) An electron capture detection method comprises generating deep-ultraviolet rays by a discharge in helium gas, generating inactive gas containing two gas components having different ionization energies from each other, supplying dopant gas generated from the dopant gas source, supplying column gas from a gas chromatographic column, ionizing the dopant gas by the deep-ultraviolet rays, and detecting a signal corresponding to a component of the column gas by recombination reaction with ionized ions.

(5) A chromatogram creating apparatus comprises a discharge chamber to which helium gas is supplied and which generates deep-ultraviolet rays by a discharge in the helium gas, and a dopant gas source accommodating inactive gas that contains two gas components having different ionization energies from each other, a detecting tube to which dopant gas is supplied from the dopant gas source, to which column gas is supplied from a gas chromatographic column, which ionizes the dopant gas by the deep-ultraviolet rays, and which detects a signal corresponding to a component of the column gas by recombination reaction with ionized ions, and a data processing unit creating a chromatogram of the sample according to a detection signal output from the detecting tube.

According to the present invention, the electron capture detector that uses the discharge in He, that can suppress generation of inverted peaks generated when current between the detection electrodes temporarily rises by ionized organic matters, that has a simple configuration, and that can ensure high sensitivity, the electron capture detection method, and the chromatogram creating apparatus having the electron capture detector can be realized.

Furthermore, the electron capture detector having the high sensitivity and the wide dynamic range without using a pulsed-discharge system that needs radioactive matters and a complicated circuit can be realized.

The conventional nonradiative electron capture detector, e.g., pulsed-discharge photoionized electron capture detector is based on the principle of ionizing dopant gas such as xenon by UV rays generated when helium excited by the discharge returns to a ground state.

In this case, the excitation of the helium by the discharge has a permitted transition from the ground state to $2^3P$, $2^1P$ or the like. Because the excited helium returns to the ground state by momentarily emitting UV rays, the life of the excited helium is as short as $10^{-9}$ to $10^{-5}$ second.

However, as shown in FIG. 9, types of the transition of helium to the excited state include the permitted transition indicated by solid lines and a forbidden transition indicated by dotted lines. The lives of the excited helium by the both transitions greatly differ.

For example, the helium having made the forbidden transition to $2^1S$ or $2^3S$ which is a metastable state, has a life of about several seconds to several minutes.

Therefore, ionization of the dopant gas in this case is considered to be a collision reaction with metastable helium (He*) (Formula (5)), which is a different mechanism from ionization by UV rays based on the permitted transition.

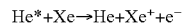

$$He^* + Xe \rightarrow He + Xe^+ + e^-$$    Formula (5)

The mechanism of ionization of the dopant gas has been theorized based on the permitted transition of He by a glow discharge in helium. Due to this, the reason for emergence of inverted peaks has not been able to be clearly studied.

The forbidden transition of helium by the glow discharge in helium is applied to the dopant-gas ionization mechanism and techniques are developed based on the theory, whereby the problem could be solved.

A component lower in ionization potential than the dopant gas is caused to coexist with the dopant gas as a Penning gas. By doing so, the performance of the nonradiative electron capture detector or particularly a detection lower limit value thereof that has been considered to be inferior to that of the radiative electron capture detector has been improved to 0.1 pg or less in absolute value. Therefore, the nonradiative electron capture detector can perform high-sensitivity analysis equivalent to or higher than that of the radiative electron capture detector.

By causing the component lower in ionization potential than the dopant gas to coexist with the dopant gas as the Penning gas, the problem of the emergence of inverted peaks that are regarded as a defect of the nonradiative electron capture detector can be solved. It is, therefore, possible to improve reliability of the nonradiative electron capture detector as a detector and use the detector in various fields.

By selecting the type of the Penning gas coexisting with the dopant gas, a specific component can be selectively detected. For example, if 3% xenon-containing helium is used as the dopant gas, acetone of the order of several hundreds of ppm is caused to coexist with the dopant gas as the Penning gas (an organic gas component lower in ionization potential than a dopant gas component). It is thereby possible to selectively detect siloxane with high sensitivity. Furthermore, the nonradiative electron capture detector can be used as a high-density selective detector for non-electron-affinic compounds, which is necessary for various fields.

It is clarified that the emergence of the inverted peaks that has been regarded as the defect of the nonradiative electron capture detector is based on an increase of current because of progress of ionization by the Penning effect produced by non-electron-affinic components dissolved from the column and because of an increase in the quantity of generated free electrons. A novel detector using the principle has been developed. The Penning effect that is the response principle of the detection occurs by an absolute amount of several tens of picograms. Therefore, the novel detector functions as a detector having considerably high sensitivity.

BRIEF DESCRIPTION OF THE DRAWINGS

FIG. 6 is a table showing ionization potentials and emission energies of matters to be contained in the dopant gas.

In FIG. 9, the life of the excited-state helium is $10^{-9}$ to $10^{-6}$ second for a permitted transition of $2^3P$, $2^1P$, $3^3S$, $3^1S$, $3^3P$, or $3^1P$ and several seconds to several minutes for a forbidden transition of $2^3S$ or $2^1S$.

FIG. 10 is gas chromatograms showing improvements in detection sensitivity by the Penning effect produced by the present invention. FIG. 10(a) is a chromatogram when acetone (300 ppm) is added, as Penning gas, to dopant gas (3% Xe/He), and FIG. 10(b) is a chromatogram created using only the dopant gas (3% Xe/He).

FIG. 11(a) is a gas chromatogram created using only the dopant gas (3% Xe/He), and FIG. 11(b) is a gas chromatogram when acetone (300 ppm) is added, as Penning gas, to dopant gas (3% Xe/He). A peak (1) is n-butanol, a peak (2) is trichloroethylene, a peak (3) is toluene, a peak (4) is octane, a peak (5) is p-xylene, and a peak (6) is n-undecane.

DESCRIPTION OF REFERENCE SYMBOLS

Figure 1:
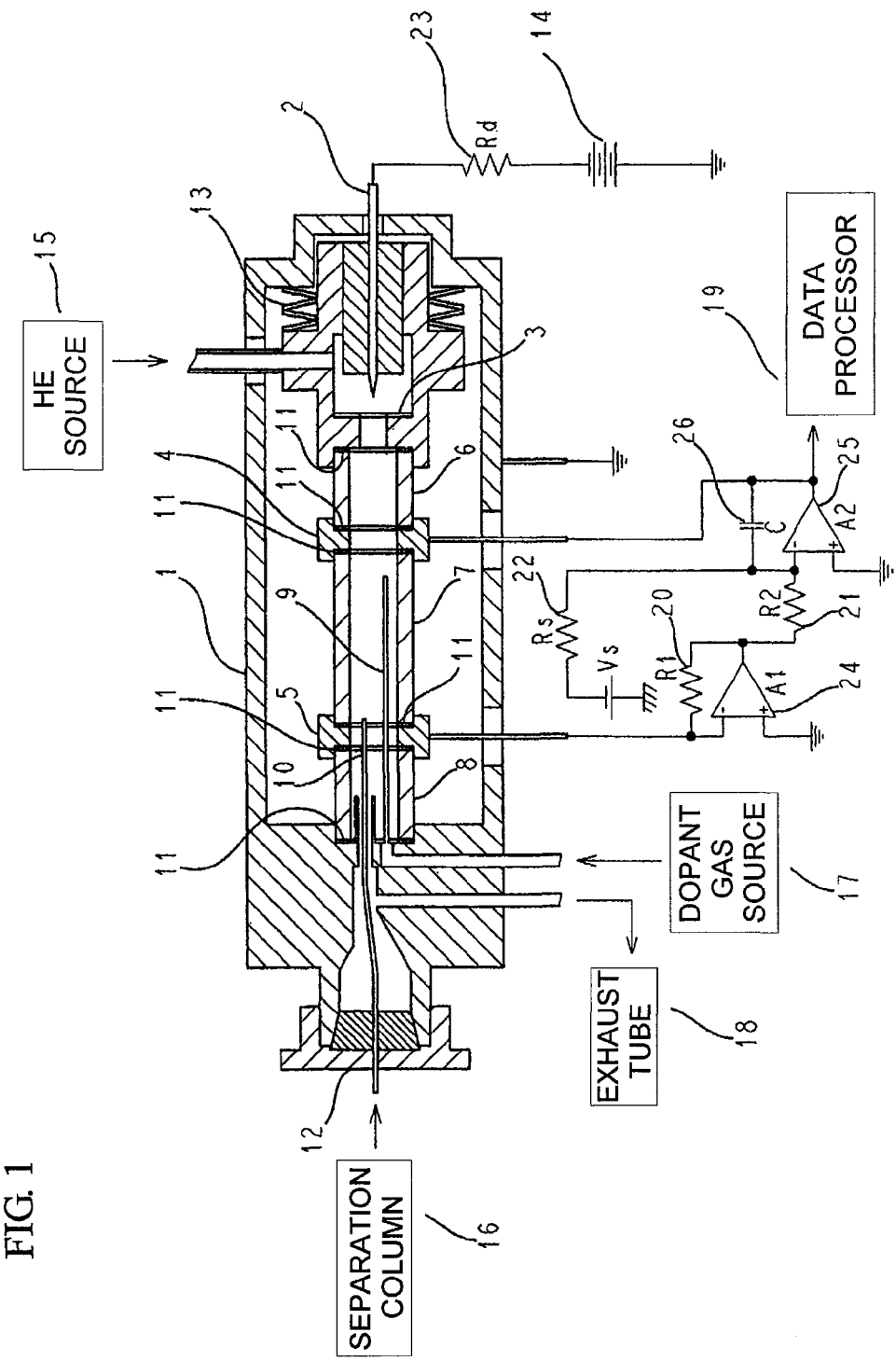
FIG. 1 is a schematic cross-sectional view of an electron capture detector according to an embodiment of the present invention.

1 . . . housing, 2-5 . . . electrode, 6-8 . . . insulating tube, 9, 10 . . . filling tube, 11 . . . flat packing, 12 . . . seal material, 13 . . . coned disc spring, 14 . . . direct-current (DC) power supply, 15 . . . He source, 16 . . . separation column, 17 . . . dopant gas source, 18 . . . exhaust tube, 19 . . . data processor, 20-23 . . . resistance, 24, 25 . . . operational amplifier, 26 . . . capacitor, 30 . . . detector circuit Best Mode for Carrying Out the Invention FIG. 1 is a schematic block diagram of an electron capture detector to which an embodiment of the present invention is applied and a schematic block diagram of a chromatogram creating apparatus having the electron capture detector. In the embodiment shown in FIG. 1, electron capture process is controlled using a direct-current (DC) continuous discharge system, and the electron capture detector having high sensitivity and wide dynamic range is constructed.

Referring to FIG. 1, a needle-like electrode 2 and a ring-shaped electrode 3 are disposed in a basically axisymmetric discharge chamber to be isolated from each other by 1 mm to 2 mm and opposed to each other. Each of the electrodes 2 and 3 is preferably made of Pt. Further, an appropriate discharge resistance and an appropriate discharge voltage are selected so that a discharge current is 0.1 mA to 2 mA.

Under the above-stated conditions, it suffices that the discharge voltage is several hundreds of volts, and if a high-voltage DC power supply 14 supplies a voltage of about 1000 V, sufficient stability and sufficient discharge current can be obtained.

A resistance Rd connected between the needle-like electrode 2 and the DC power supply 14 may be sufficiently higher than a differential negative resistance between the discharge voltage and the discharge current. According to the embodiment of the present invention, an applied voltage is preferably about a half of the voltage from the high-voltage DC power supply 14.

In the DC discharge generated by the system according to the embodiment, if the discharge current rises to be equal to or higher than several tens of milliamperes, then a shape of the needle electrode 2 is changed, and long-term stable discharge current cannot be obtained.

The discharge is generated while the electrode 2 serves as a negative electrode and the electrode 3 serves as a positive electrode, and the electrode 3 is made electrically in a conducting sate with a housing 1 and grounded so that the electrode 3 has zero potential. The reason for grounding the electrode 3 is to allow the electrode 3 to function as a guard ring shielding a high voltage part from a detecting tube using weak current.

An electron capture detector for a gas chromatography even in high-temperature use, in particular, deals with high voltage and weak current of the pA order at temperature of 250° C. to 400° C. Due to this, none of insulating materials are sufficient in performance.

A He source 15 is arranged upstream of a needlepoint of the needle-like discharge electrode 2 so as to supply fresh He to a discharge unit. The He source 15 supplies He at a sufficient flow rate of, for example 20 cm3/min to 60 cm3/min to a discharge chamber.

The He activated by the discharge between the needle electrode 2 and the ring-shaped electrode 3 is introduced into a detecting tube that includes an insulating tube 6, a ring electrode 4, an insulating tube 7, a ring electrode 5, and an insulating tube 8 arranged coaxially with the discharge chamber.

While the activated He is considered to be in a $He_2$ state, a life of the activated He is relatively long and the activated He, therefore, flows to move and diffuse. As a result, an emission center of deep-UV rays is located slightly downstream of the discharge electrodes 2 and 3.

To cause light emission upstream of a dopant gas layer (on He-supply side), it is necessary to set an isolation distance between the electrodes 3 and 4 to about more than a threefold of an inside diameter of the detecting tube although it depends on the flow rate.

Figure 2:
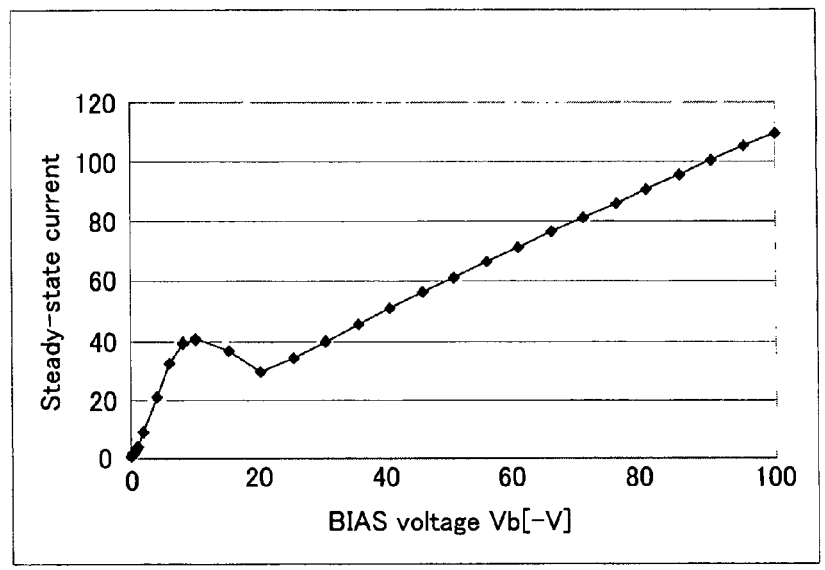
FIG. 2 is a graph showing the relationship between bias voltage and steady-state current when a discharge electrode is proximate to a bias electrode.

If the isolation distance between the electrodes 3 and 4 is insufficiently short, abnormal characteristic between bias voltage Vb and steady-state current Is, as shown in FIG. 2 to be described later, emerge.

If the isolation distance between the electrodes 3 and 4 is excessively long, then an intensity of the deep-UV rays is lessened because of the long distance of deep-UV rays to the dopant gas layer and sufficient steady-state current cannot be obtained. The discharge current is inversely proportional to about a square of the isolation distance. Because the discharge current cannot be greatly increased in the DC continuous discharge system, it is a practical choice to set the isolation distance between the electrodes 3 and 4 to be equal to or smaller than 20 times as large as the diameter of the detecting tube.

Because a gas chromatographic apparatus also detects high-boiling compounds, a temperature of the detecting tube is often kept as high as 200° C. to 400° C. as well as at room temperature. Furthermore, because the gas chromatographic apparatus mainly detects halogen compounds in only the tiniest traces of pg, the insulating tubes need to have smaller amounts of adsorption and to keep isolation between the electrodes at high temperature.

Due to this, an inactive material having good electric property such as quartz or transparent alumina that are well-known means is flattened and smoothed to be used for the insulating tubes. Further, washer-like flat packings 11 made of inactive soft metal such as Au, Ag or Al are used to ensure airtightness between the insulating tubes 6, 7, and 8 and the electrodes 3, 4, and 5.

The reason for adopting the way mentioned above is as follows. Because of large difference between the insulating material and the electrode material in coefficient of expansion and exposure of the insulating tubes 6, 7, and 8 and the electrodes 3, 4, and 5 to strong UV rays from the active He, it is difficult to seal the insulating tubes 6, 7, and 8 from the electrodes 3, 4, and 5 using organic materials. Further, to deal with the axial difference in coefficient of expansion, an axially displaceable slide mechanism is provided and a coned disc spring 13 is inserted between the housing 1 and the discharge chamber, thereby allowing the discharge chamber and the detecting tube in their entirety to have a structure capable of preventing damage caused by thermal stress while keeping airtightness.

A filling tube 9 is opened in an upward direction (toward He-supply side) downstream of or near the ring electrode 4. He-based dopant gas containing two or more gas components having ionization energies lower than that of He and different from each other, e.g., inorganic gas such as several percent of Xe or $CO_2$ and organic gas such as acetone or toluene is introduced via the filling tube 9 from a dopant gas source 17.

Although the dopant gas also diffuses upward against gas flow, a concentration of the dopant gas is reduced by one digit as the dopant gas diffuses 1 mm to 3 mm upward. The filling tube 9 has a diameter sufficiently smaller than that of the detecting tube and a lower flow rate than that of He.

Due to this, the dopant gas blowing from the filling tube 9 does not blow up as compared with the diameter of the detecting tube, and a layer of high-concentration dopant gas almost uniform in diameter direction is formed downstream of the electrode 4. This gas layer absorbs deep-UV rays, thereby forming plasma of low-concentration dopant gas.

The dopant gas layer absorbs deep-UV rays from He and has such a concentration and a thickness as to be completely absorbed near the ring electrode 5. Negative bias voltage is applied to the ring electrode 4 near upstream of this gas layer. Therefore, even positive ions having low mobility are partially attracted toward the electrode 4, and electron density is higher near upstream of the electrode 5. Needless to say, the positive ions of the dopant gas are present in this area.

While the plasma generated on the upstream side of the ring electrode 4 acts as reactive current flowing between the electrodes 2 and 4, an opening of the filling tube 9 can be disposed up to slightly upstream of the electrode 4.

According to the result of an experiment conducted by the applicant of the present invention, it is estimated that the distance between the opening of the filling tube 9 and the electrode 4 needs to be equal to or larger than the diameter of the detecting tube in order that the deep-UV rays are completely absorbed.

The ring electrode 5 is grounded virtually as a circuit and has zero potential, so that the potential of the ring electrode 5 is positive relative to that of the electrode 4 to which negative voltage is applied. Electrons are captured by the electrode 5, so that current at which no detection target gas is present, i.e., steady-state current can be observed.

When deep-UV rays from the active He reaches a space in which this electron capture reaction occurs, the detection target gas is directly ionized and the current flowing through the ring electrode 5 rises. As result, inverted peaks may possibly emerge.

However, according to the present invention, because of the presence of the dopant gas to be described later, the deep-UV rays from the He activated by the discharge are shielded by the dopant gas layer, whereby halogen compound gas is not directly ionized to suppress generation of the inverted peak.

As shown in FIG. 2, the relationship between the absolute value of the bias voltage of the discharge chamber and the detecting tube and the steady-state current has a tendency of rising once, falling, and rising again even if the position of the opening of the filling tube 9 is changed when the distance between the bias ring electrode 5 and the ring electrode 3 is small. If the distance between the electrode 5 and the ring electrode 3 is appropriately set, the relationship has a convex-upward gradually monotonous increase as shown in FIG. 3.

Figure 3:
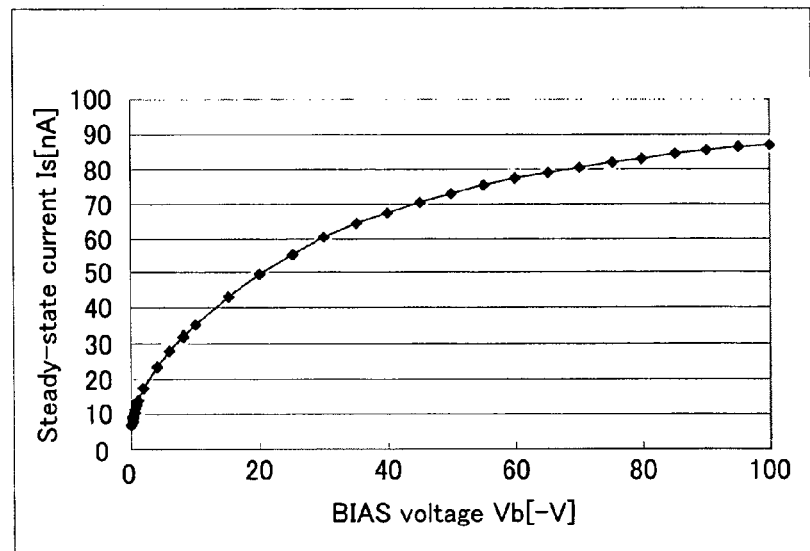
FIG. 3 is a graph showing the relationship between bias voltage and steady-state current in a preferred electrode arrangement.

To acquire the monotonous increase characteristic as shown in FIG. 3 is an essential condition for controlling the bias voltage applied to the ring electrode 4. If the distance between the electrode 5 and the electrode 3 is excessively long, plasma density lowers and the steady-state current lowers.

Referring to FIG. 1, the filling tube 10 is fixed to the housing 1 by seal material 12, opened toward upstream in a portion which introduces the gas passed through and separated from a separation column 16 into the detecting tube between the ring electrodes 5 and 4. A tip end of the filling tube 10 is located downstream of the opening of the filling tube 9.

The filling tubes 9 and 10 are not necessarily coaxial with the detecting tube. Rather, if the filling tubes 9 and 10 are slightly eccentric to the detecting tube, a filling-tube holding structure can be made simpler. In this way, even if the tubes are not completely axisymmetric, the gas also diffuses in the diameter direction of the detecting tubes. Therefore, the almost axially uniform gas layer is formed.

When gaseous halogen compound-based gas is emitted from the filling tube 10, a gas layer containing the halogen compounds is formed in layers near the opening of the filling tube 10 on the downstream side of the dopant gas layer. Since this region is a part having high electron density, the halogen compounds promptly capture electrons, thereby turning into negative ions.

Furthermore, the deep-UV rays from the $He_2$ are simultaneously shielded by the dopant gas layer, so that only the electron capture and recombination processes are performed in this region without directly ionizing the gas containing the halogen compounds.

A collision cross-section of positive ions against negative ions is larger by several digits than that of positive ions against electrons, and most parts of negative ions recombine with positive ions to reduce electron current in the ring electrode 5.

A signal current from the electrode 5 is supplied to an inverted input terminal of an operational amplifier 24, and converted into voltage by the operational amplifier 24. An output signal of the operational amplifier 24 is supplied via a resistance 20 to an input terminal of the same operational amplifier 24 and also supplied to an inverted input terminal of an amplifier 25 via a resistance 21. The output signal supplied to the inverted input terminal of the amplifier 25 is compared with a reference signal (current generated by a voltage source Vs and a resistance 22).

An output signal of the amplifier 25 is supplied to an input terminal of the same amplifier 25 via a capacitor 25 and also supplied to the electrode 4.

If the signal current from the electrode 5 is to be lowered, then the absolute value of the bias voltage is increased by the output signal of the control amplifier 25, and operation for keeping the current of the ring electrode 5 constant is performed.

Figure 5:
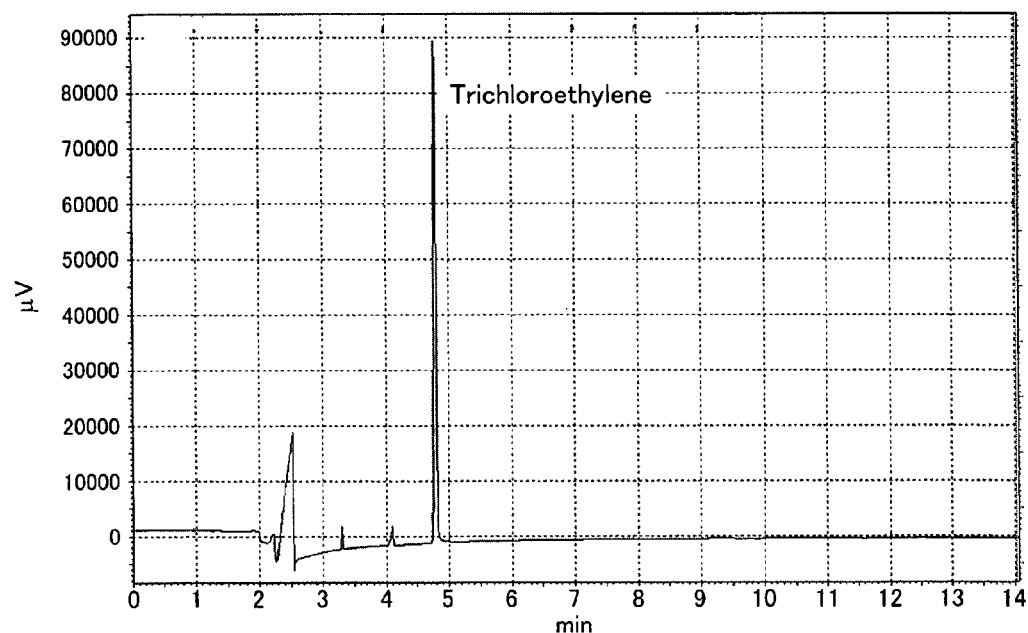
FIG. 5 is a graph showing a chromatogram obtained by the electron capture detector when the number of types of electron products contained in dopant gas is two.

Moreover, the output signal of the control amplifier 25 is output to a data processor 19. The data processor 19 performs data processing on the output signal of the control amplifier 25, and calculates a detection result as shown in FIG. 5. The detection result is displayed by image display means or printed out by printing means.

If the characteristic between the bias voltage and the steady-state current is that as shown in FIG. 3, then an electric field is intensified as the absolute value of the bias voltage is higher, and effective areas of the ring electrodes 4 and 5 increase. Therefore, the steady-state current rises per se and the density of electrons with which the halogen compounds is to combine rises.

As a result, it is possible to maintain the electron capture reaction even for the gas containing the concentrated halogen compounds. If a signal corresponding to the bias voltage output is chromatographically output, the detector having a wide dynamic range can be realized.

If such control is performed with the characteristic shown in FIG. 2, the bias voltage is controlled discontinuously in the region in which the steady-state current decreases relative to the increase of the absolute value of the bias voltage. As a result, an ordinary chromatograph is not obtained practically.

In this manner, linearization similar to pulse sampling performed by the radiative electron capture detector is performed entirely by a DC circuit. Because the bias-control amplifier 25 acts as an integrator, the current from the ring electrode 5 at this time is substantially kept constant without variation.

Unless such control is performed, then detected current falls to several to several tens of percent when 10 pg of $CCl_4$ is introduced from the filling tube 10, the density of to-be-captured electrons decreases, thus showing considerably high nonlinearity. This results in strict restriction on the practical dynamic range.

Furthermore, organic matters in a sample are not directly ionized by the deep-UV rays from He activated by the discharge. However, if the dopant gas contains only one type of electron product, the organic matters in the sample are ionized by energy of the electron product, e.g., Xe or $CO_2$ activated by the energy of the activated He.

Figure 4:
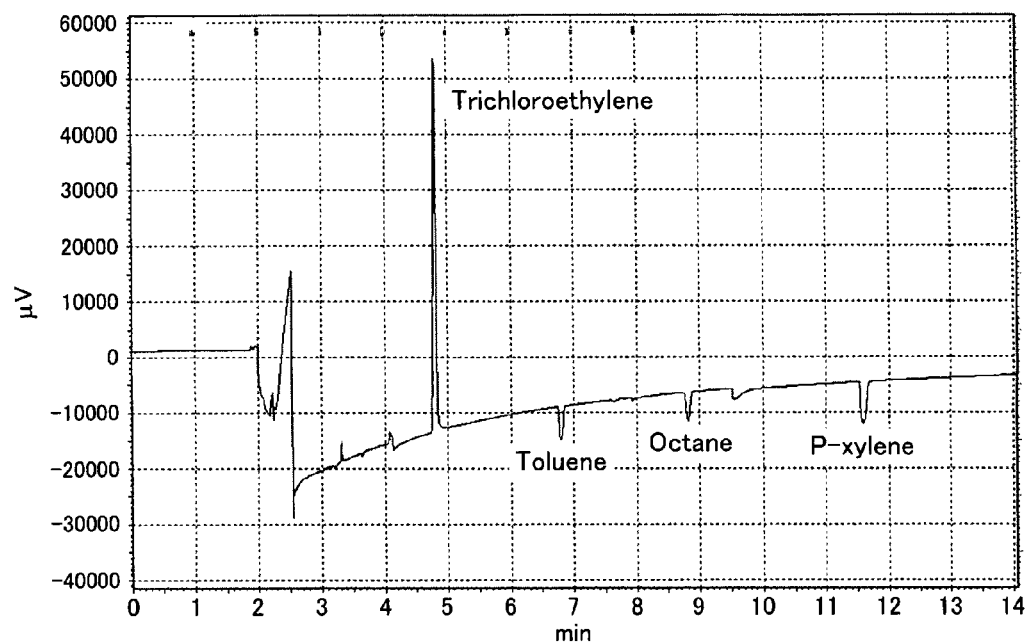
FIG. 4 is a graph showing a chromatogram obtained by the electron capture detector when the number of types of electron products contained in dopant gas is one.

Due to this, the ionized organic matters temporarily increase the current between the detection electrodes. As a result, inverted peaks (of toluene, octane, and P-xylene) are detected on the chromatogram as shown in FIG. 4.

As means for suppressing generation of these inverted peaks, two or more components different in ionization energy are used as electron products contained in the dopant gas.

If the electron products contained in the dopant gas are the two or more components, the ionization energy emitted from the electron product, e.g., Xe or $CO_2$ having the higher ionization energy is consumed to ionize trace organic gas of the electron product such as several ppm to several percent of acetone, toluene, and amine having the lower ionization energy. Therefore, the energy for ionizing the organic matters in the sample hardly remains.

Moreover, the ionization energy emitted from the electro product having the lower ionization energy does not have intensity necessary to ionize the organic matters. Therefore, the organic matters in the sample are not ionized, either.

As a result, the ionized organic matters do not temporarily increase the current between the detection electrodes, and the inverted peaks shown in FIG. 5 are hardly detected on the chromatogram.

Combination and concentrations of the two or more electron products to be contained in the dopant gas will next be described.

First of all, ionization energy values of the respective electron products are important. FIG. 6 is a table showing the ionization energy of two or more electron products to be contained in the dopant gas.

The ionization energy of the electron product having the higher ionization energy needs to be lower than the emission energy of He so that the electron capture detector functions properly.

Moreover, the ionization energy of the electron product having the lower ionization energy needs to be lower than the emission energy of the electron product having the higher ionization energy.

Furthermore, if the emission energy of the electron product having the lower ionization energy is higher than the ionization energy of the organic matters in the sample, it is necessary to add an electron product having lower emission energy to the dopant gas. Nevertheless, if the electron product having the lower ionization energy and the emission energy lower than the ionization energy of the organic matters in the sample is selected, there is no need to add the electron product having the lower emission energy.

Next, as regards the concentrations of the electron products contained in the dopant gas, if the concentration of the electron product having the higher ionization energy is too low, then electrons to be generated are insufficient in quantity, and electron capture is performed only insufficiently.

Conversely, if the concentration of the electron product having the higher ionization energy is too high, then the emitted energy increases, and the electron product having the lower ionization energy in large quantities is necessary.

On the other hand, as regards the electron products having the lower ionization energy, if its concentration is too low, then absorption (consumption) of the energy emitted from the electron product having the higher ionization energy is insufficient, and the generation of the inverted peaks cannot be, therefore, suppressed.

A measurement experiment was conducted using a combination of several percent of Xe and several ppm of acetone in view of stability of concentration control and influence on human bodies and environment. FIG. 5 is a graph showing a result of the experiment. As shown in FIG. 5, a chromatogram in a form characteristic of the electron capture detector and without inverted peaks was obtained.

The chromatogram shown in FIG. 5 is displayed as an image by display means of the data processor 19 or printed out by printing means.

In FIG. 6, the emission energy of Xe is 9.6 eV whereas the ionization energy of acetone is 9.72 eV. Theoretically, therefore, acetone is not ionized. Actually, however, the inverted peaks disappear. The reason is estimated as follows. The emission energy of Xe is considered to be absorbed (consumed), so that the value of each energy shown in FIG. 6 is not a one point value but an average of values having a certain width. Even if the ionization energy of the electron product having the lower ionization energy is slightly higher than the emission energy of the electron product having the higher ionization energy, the emission energy of the electron product having the higher ionization energy is sufficiently absorbed (consumed) by increasing the amount of the electron product having the lower ionization energy.

In this case, among the matters shown in FIG. 6, electron products having higher ionization energies are matters having ionization energies equal to or higher than 12.0 eV, and electron matters having lower ionization energies are gasifiable matters having ionization energies equal to or lower than 11.0 eV.

The two or more electron products to be contained in the dopant gas may be supplied to the dopant gas by mixing them with inactive gas serving as base gas, e.g., He in one cylinder in advance, or each of the electron products is mixed with the inactive gas that is the base gas, and these mixtures may be mixed together when the dopant gas is introduced into the detector.

Furthermore, column gas completed with reaction is discharged together with the discharge He gas and the dopant gas from an exhaust tube 18 located on most downstream side.

Figure 7:
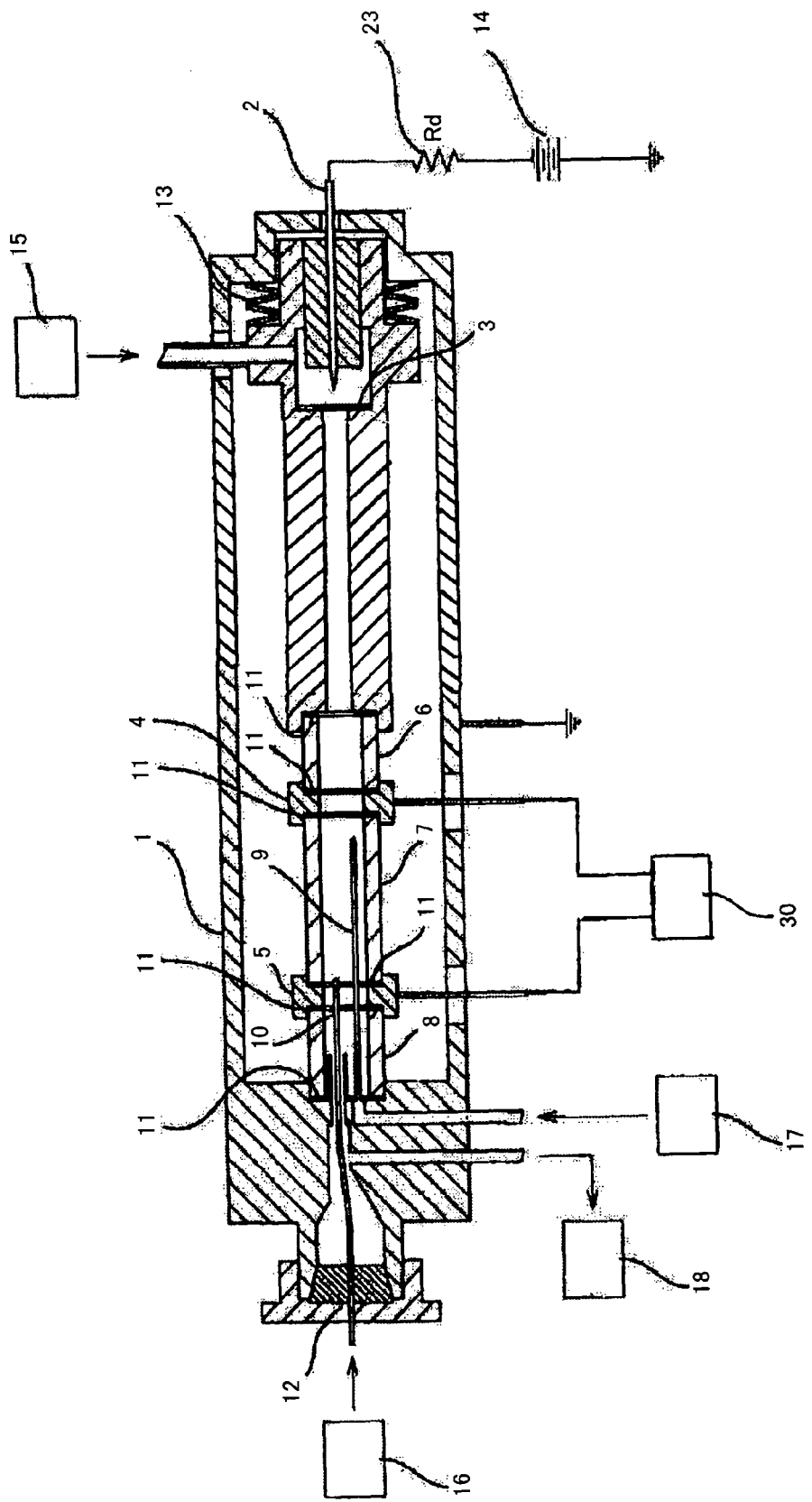
FIG. 7 is a cross-sectional view of a nonradiative electron capture detector according to an embodiment of the present invention.
Figure 8:
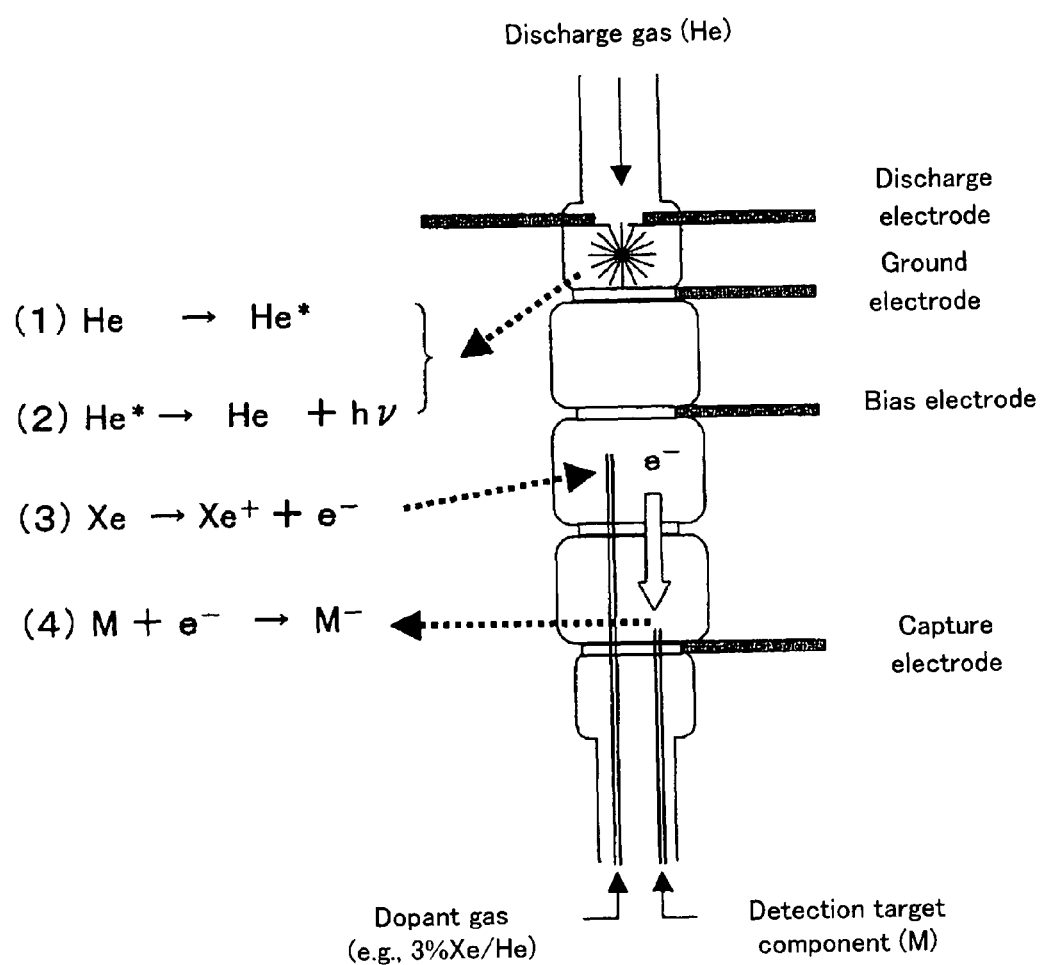
FIG. 8 is a schematic diagram for explaining a conventional nonradiative electron capture detector.
Figure 9:
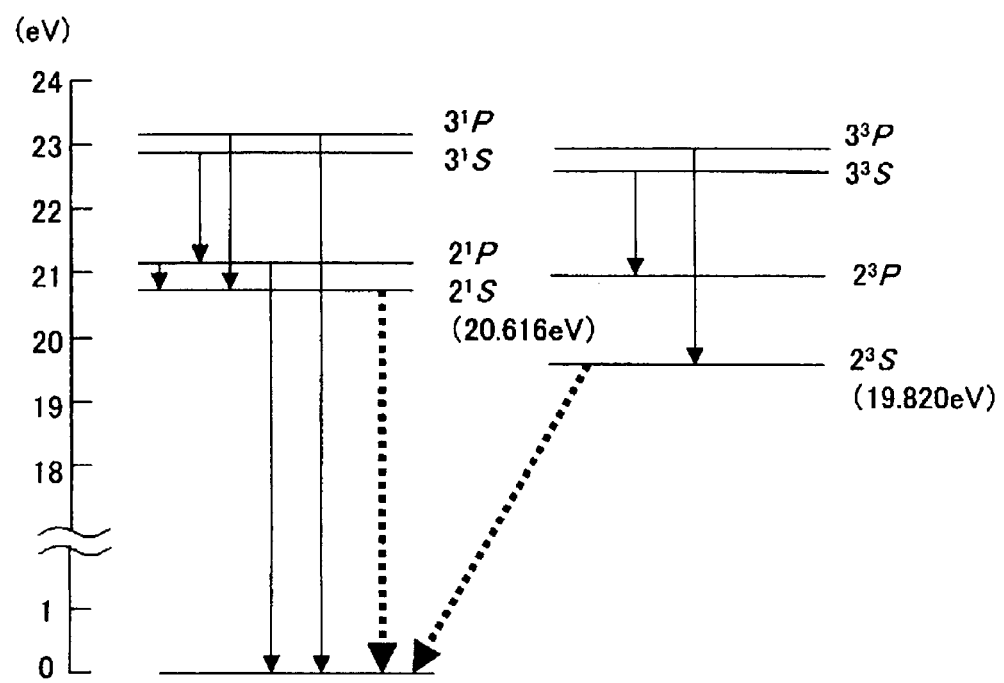
FIG. 9 is a schematic diagram for explaining a life of an excited-state helium due to glow discharge.

FIG. 7 is a cross-sectional view of a nonradiative electron capture detector according to an embodiment of the present invention. The detector is constructed by a discharge chamber that includes a needle-like electrode 2 and a ring-shape electrode 3 in a housing, and a detecting tube having an insulating tube 6, a ring electrode 4, an insulating tube 7, a ring electrode 5, and an insulating tube 8 sequentially arranged downstream of the discharge chamber. Helium is introduced into the discharge chamber, and stable glow discharge is generated between the two electrodes by a DC power supply and a series resistance.

In the detecting tube, a filling tube 9 opened upstream to introduce an organic gas component that provokes the Penning effect into helium and dopant gas including xenon, argon or the like serving as the dopant gas, and a filling tube 10 opened upstream to introduce a detection target component dissolved from a gas chromatographic column are disposed in the detecting tube. An opening of the filling tube 10 is located between the ring electrodes 4 and 5 and downstream of the filling tube 9.

In the nonradiative electron capture detector according to the present invention, the inactive gas such as xenon or argon ordinarily used in the process of ionizing the dopant gas and the organic gas serving as Penning gas coexist. Due to this, if an isolation distance between the electrodes 3 and 4 is short, the organic gas possibly contaminates the discharge chamber.

Therefore, in the present detector, the isolation distance between the electrodes 3 and 4 is set to about ten times or more as large as an inside diameter of the detecting tube. However, if the isolation distance is too long, a volume of the detecting tube increases. As a result, a density of metastable excited helium generated by the discharge decreases, thus deteriorating ionization efficiency.

In the DC continuous discharge system, it is inappropriate to greatly increase discharge current for increasing the amount of metastable excited helium. The isolation distance is, therefore, set to be equal to or smaller than 30 times as large as the inside diameter of the detecting tube at largest. Further, because the needle-like electrode possibly degrades due to contamination of the discharge chamber, a discharge unit is made detachable to prevent the possible degradation.

The organic compound is added, as the Penning gas, to the dopant gas, and the ionization potential of the dopant gas is lowered by the Penning effect provoked by the organic compound, whereby the ionization efficiency is thereby improved. At the same time, by suppressing kinetic energy of generated free electrons to be low, efficiency for the electron capture reaction using an electron-affinic detection target component dissolved from the column is enhanced. By doing so, detection sensitivity of the nonradiative electron capture detector is improved.

Specifically, if about 300 ppm of an organic compound such as triethylamine, acetone or tetramethyldisiloxane that produces the Penning effect, for example, is added to 3% xenon-containing helium normally used as the dopant gas of the nonradiative electron capture detector, the detection sensitivity has marked improvement.

FIG. 10 shows chromatograms of γ-BHC both in the case that the Penning gas is not added to 3% xenon-containing helium and in the case that the Penning gas is added to 3% xenon-containing helium, respectively. Detection limit values of γ-BHC are measured from the respective chromatograms. In the case of Penning gas free, the detection limit value is 10 pg (S/N=3). In the case of adding the Penning gas, the detection limit value is 0.08 pg (S/N=3). Namely, if acetone is added to 3% xenon-containing helium, the detection sensitivity is improved to be 100 times or more as high as the detection sensitivity in the case that acetone is not added.

The inverted peaks are simultaneously eliminated along with considerable improvement in the detection sensitivity attained by adding the Penning gas to the dopant gas. That is, if the Penning gas is added to ordinary dopant gas, the inverted peaks that have emerged thus far disappear from the chromatogram.

The reason is as follows. The ordinary dopant gas to which the Penning gas is not added has high ionization potential, e.g., 12.1 eV for xenon. Due to this, the ionization potential of the detection target component dissolved from the gas chromatographic column and introduced into the detecting tube from the filling tube 10 shown in FIG. 7 is lower than that of xenon, the ionization efficiency is improved by the Penning effect. As a result, the quantity of generated free electrons increases and the ground current in the detector rises.

The response principle of the electron capture detector is the electron capture reaction caused by the electron-affinic compound, i.e., reduction of the ground current flowing through the detector. Therefore, the increase of current emerges as the inverted peaks.

Figure 11:
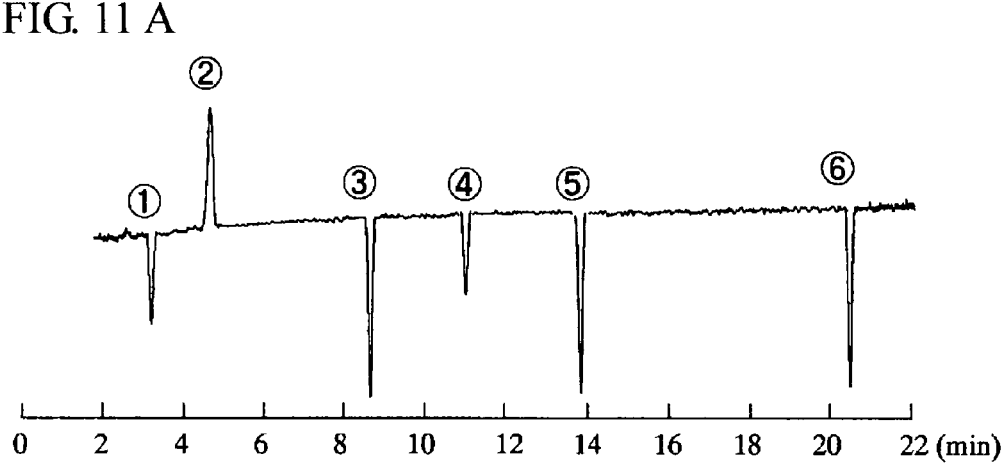
FIG. 11 is gas chromatograms showing elimination of inverted peaks due to the effect of the present invention.
Figure 11:
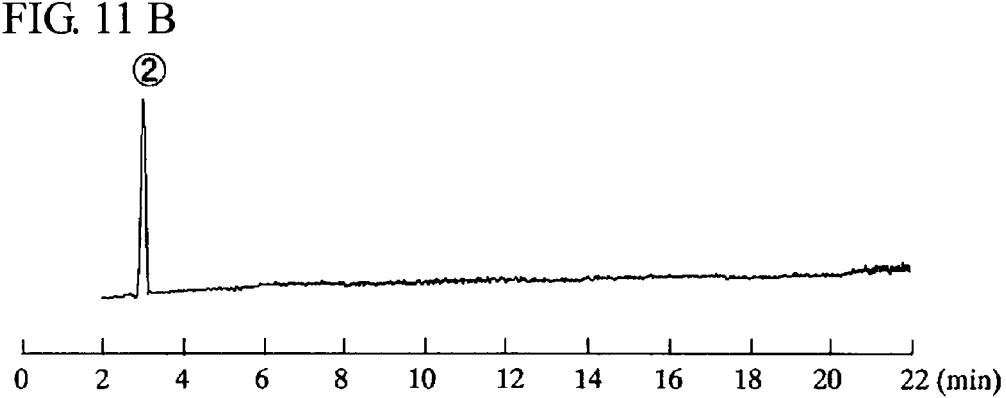

FIG. 11 shows a specific example of the above-stated respect. If the Penning gas is not added, non-electron-affinic compounds such as n-butanol, toluene, octane, p-xylene, and n-undecane emerge as the inverted peaks, respectively.

On the other hand, acetone the ionization potential of which is either equivalent or equal to or lower than those of the inverted peak compounds is caused to coexist, as the Penning gas, with the dopant gas while acetone concentration is set to about 300 ppm, the inverted peaks disappear. Although trichloroethylene serving as the electron-affinic compound emerges as a normal peak despite presence or absence of acetone serving as the Penning gas, the detection sensitivity is higher when acetone coexists with the dopant gas due to the Penning effect.

The effect of the Penning gas is quite effective not only to improve the sensitivity and eliminate the inverted peaks but also to allow the nonradiative electron capture detector according to the present invention to function as a selective detector for a specific compound group.

The ionization potential associates with molecular structure. Therefore, if a non-electron-affinic congener the ionization potential of which falls within a certain range is an analysis target, and an organic compound having an ionization potential slightly higher than the highest ionization potential of the congener is added, as the Penning gas, to the dopant gas, it is possible to cause the congener to selectively emerge as an inverted peak.

In other words, a non-electron-affinic congener higher in ionization potential than the Penning gas does not emerge as an inverted peak.

On the other hand, a non-electron-affinic compound lower in ionization potential than the Penning gas improves the ionization efficiency by the further Penning effect produced by the compound. Therefore, an inverted peak emerges.

Figure 12:
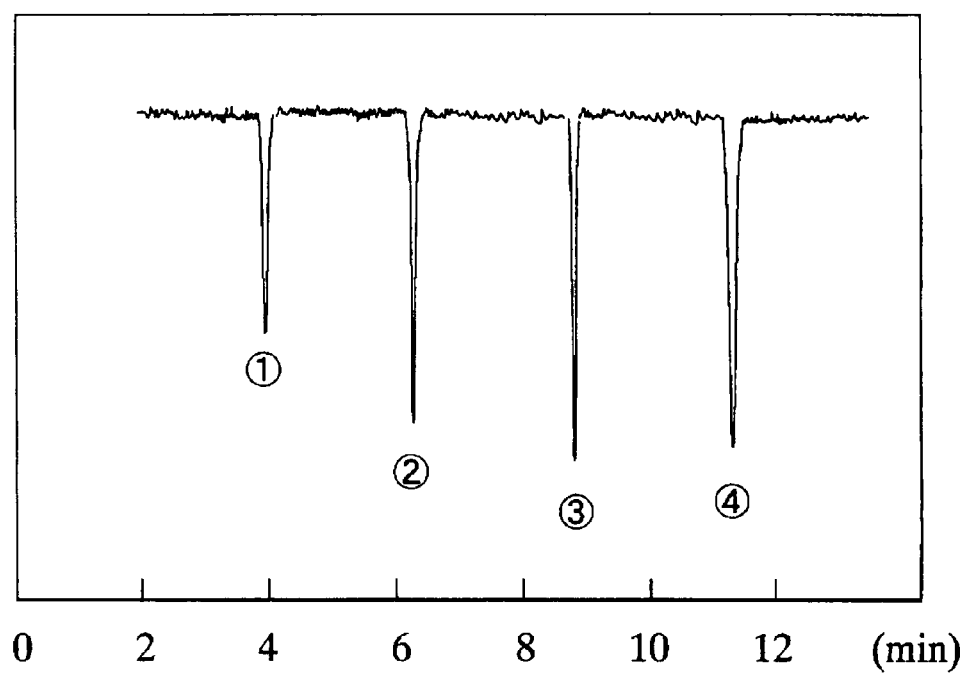
FIG. 12 is a gas chromatogram showing that a specific non-electron-affinic compound group (siloxanes) can be selectively detected by the Penning effect produced by the present invention. Dopant gas is 3% Xe/He and Penning gas is acetone (300 ppm). A peak (1) is hexamethylcyclosiloxane, a peak (2) is octamethylcyclosiloxane, a peak (3) is decamethylcyclosiloxane, and a peak (4) is dodecamethylcyclosiloxane. An injection volume of each sample is 100 pg.

For example, if about 300 ppm of acetone is mixed, as the Penning gas, with 3% xenon/helium serving as ordinary dopant gas, the non-electron-affinic compounds such as n-butanol, toluene, octane, p-xylene, and n-undecane do not emerge on the chromatogram as shown in FIG. 11 but siloxanes emerge as inverted peaks as shown in FIG. 12.

Accordingly, by selecting a Penning gas, a specific compound group can be selectively detected. In this case, if tetramethyldisiloxane or the like is used as the Penning gas, inverted peaks of the siloxanes disappear.

The present detector functions as the electron capture detector based on the phenomenon of the ground current by electron capture reaction in the case that the component dissolved from the separation column is an electron-affinic compound.

On the other hand, if the component dissolved from the separation columns are a non-electron-affinic compound, the ground current is increased by the Penning effect of the dissolved compound on the dopant gas. Due to this, the non-electron-affinic compound emerges as an inverted peak.

The present invention has clarified that the reason for emergence of this inverted peak is the Penning effect, and enables using the Penning effect as the detection principle of detecting the non-electron-affinic compound. The Penning effect on the ionization of xenon or argon serving as the dopant gas component is provoked by the non-electron-affinic compound in only the tiniest trace. Therefore, the detection sensitivity for detecting the non-electron-affinic compound based on the Penning effect is quite high.

Figure 13:
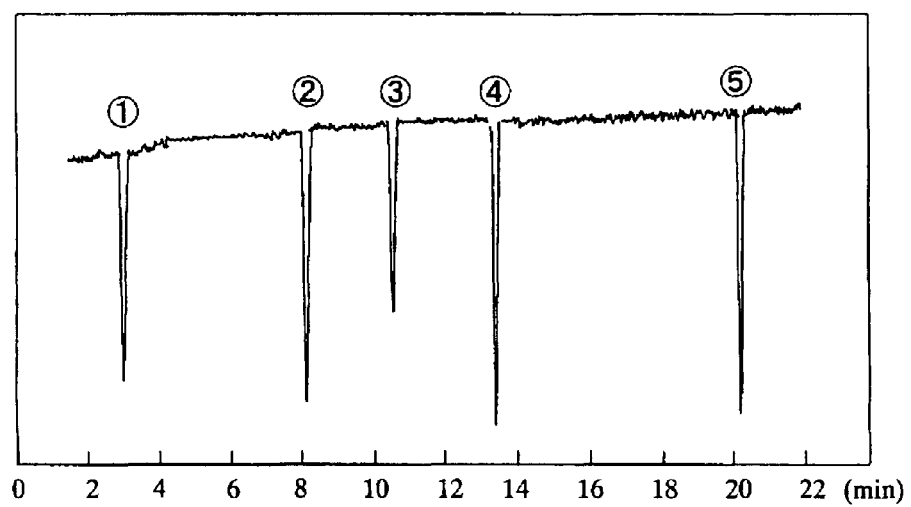
FIG. 13 is a gas chromatogram showing that non-electron-affinic compounds can be detected with high sensitivity by the Penning effect produced by the present invention. Dopant gas is 3% Xe/He. A peak (1) is n-butanol, a peak (2) is toluene, a peak (3) is octane, a peak (4) is p-xylene, and a peak (5) is n-undecane. An injection volume of each sample is 20 pg.

As shown in FIG. 13, the chromatogram can be obtained for n-butanol, toluene, octane, p-xylene, n-undecane, and the like each of which has an absolute amount of the order of several tens of picograms. The sensitivity is more than 100 times as high as that of a hydrogen flame ionization detector or the like.

Gas chromatogram detectors do not at all use the principle that the non-electron-affinic compound responds based on the Penning effect. Therefore, the principle can be used as the detection principle of a novel detector for non-electron-affinic compounds.

The present invention includes two functions, i.e., a detection function of detecting non-electron-affinic compounds based on such Penning effect, and a detection function of detecting electron-affinic compounds based on the electron capture reaction.

The invention claimed is:

1. A nonradiative electron capture detector, comprising:
a discharge chamber having a needle-like electrode and a ring-shaped electrode opposed to each other and configured to introduce helium thereinto as discharge gas to generate a DC type glow discharge between the needle-like electrode and the ring-shaped electrode, with a transport tube for transporting positively and negatively charged particles and metastable helium generated in the discharge chamber being connected to the discharge chamber;
a dopant-gas supply mechanism connected to the transport tube, and supplying dopant gas having an ionization energy lower than an emission energy of the metastable helium;
a mechanism including positive and negative electrodes, and measuring a current; and
a detecting unit measuring the current whose carriers are free electrons and positive ions generated by Penning ionization caused by a collision between the metastable helium and the dopant gas, wherein
Penning gas comprised of organic gas lower in ionization potential than dopant is caused to coexist with the dopant gas, and
an isolation distance between the needle-like electrode and the ring-shaped electrode is 10 to 30 times larger than an inside diameter of the detecting unit.

2. The nonradiative electron capture detector according to claim 1, wherein the Penning gas is an organic compound.

3. The nonradiative electron capture detector according to claim 2, wherein the organic compound is one of triethylamine, acetone or tetramethydisiloxane.

4. The nonradiative electron capture detector according to claim 1, wherein the Penning gas is added to the dopant gas to be about 300 ppm.

5. A nonradiative electron capture detector, comprising:
a discharge chamber having a needle-like electrode and a ring-shaped electrode opposed to each other and configured to introduce helium thereinto as discharge gas to generate a DC type glow discharge between the needle-like electrode and the ring-shaped electrode, with a transport tube for transporting positively and negatively charged particles and metastable helium generated in the discharge chamber being connected to the discharge chamber;

a dopant-gas supply mechanism connected to the transport tube, and supplying dopant gas having an ionization energy lower than an emission energy of the metastable helium;
a mechanism including positive and negative electrodes, and measuring a current;
a detecting unit measuring the current whose carriers are free electrons and positive ions generated by Penning ionization caused by a collision between the metastable helium and the dopant gas; and
Penning gas comprised of organic gas lower in ionization potential than dopant is caused to coexist with the dopant gas, wherein
the dopant gas is one of xenon, argon, and carbon dioxide having an ionization potential equal to or higher than 12 eV, and an ionization potential of the organic gas caused to coexist with the dopant gas is equal to or lower than 11 eV, and
an isolation distance between the needle-like electrode and the ring-shaped electrode is 10 to 30 times larger than an inside diameter of the detecting unit.

6. The nonradiative electron capture detector according to claim 5, wherein the Penning gas is an organic compound.

7. The nonradiative electron capture detector according to claim 6, wherein the organic compound is one of triethylamine, acetone or tetramethydisiloxane.

8. The nonradiative electron capture detector according to claim 5, wherein the Penning gas is added to the dopant gas to be about 300 ppm.

* * * * *